(12) United States Patent
Wadstein et al.

(10) Patent No.: US 7,947,737 B1
(45) Date of Patent: May 24, 2011

(54) METHOD OF TREATING HYPERTENSION AND REDUCING SERUM LIPASE ACTIVITY

(75) Inventors: Jan Wadstein, Volda (NO); Jan Remmereit, Oslo (NO)

(73) Assignee: Aker Biomarine ASA, Oslo (NO)

( * ) Notice: Subject to any disclaimer, the term of this patent is extended or adjusted under 35 U.S.C. 154(b) by 764 days.

(21) Appl. No.: 09/410,484

(22) Filed: Sep. 30, 1999

(51) Int. Cl.
*A61K 31/20* (2006.01)
*A61K 47/12* (2006.01)
*A61K 31/19* (2006.01)
*A01N 37/00* (2006.01)

(52) U.S. Cl. ......... 514/560; 424/439; 514/557; 514/558
(58) Field of Classification Search .................. 514/560, 514/558; 424/439
See application file for complete search history.

(56) References Cited

U.S. PATENT DOCUMENTS

| | | | | |
|---|---|---|---|---|
| 3,729,379 | A | 4/1973 | Emken | 195/30 |
| 4,474,773 | A * | 10/1984 | Shinitzky et al. | 514/78 |
| 5,208,356 | A | 5/1993 | Pariza et al. | 554/79 |
| 5,428,072 | A | 6/1995 | Cook et al. | 514/560 |
| 5,430,066 | A | 7/1995 | Cook et al. | 514/560 |
| 5,554,646 | A | 9/1996 | Cook et al. | 514/560 |
| 5,585,400 | A | 12/1996 | Cook et al. | 514/560 |
| 5,674,901 | A | 10/1997 | Cook et al. | 514/558 |
| 5,760,082 | A | 6/1998 | Cook et al. | 514/560 |
| 5,804,210 | A | 9/1998 | Cook et al. | 424/440 |
| 5,814,663 | A | 9/1998 | Cook et al. | 514/560 |
| 5,827,885 | A | 10/1998 | Cook et al. | 514/558 |
| 5,851,572 | A | 12/1998 | Cook et al. | 426/2 |
| 5,855,917 | A | 1/1999 | Cook et al. | 424/502 |
| 5,856,149 | A | 1/1999 | Pariza et al. | 435/134 |
| 7,157,496 | B2 * | 1/2007 | Kamegai et al. | 514/560 |

FOREIGN PATENT DOCUMENTS

| | | |
|---|---|---|
| EP | 440352 | 8/1991 |
| EP | 779033 | 6/1997 |
| EP | 839897 | 5/1998 |
| JP | 63036744 A * | 2/1988 |
| WO | WO 97/18320 | 5/1997 |
| WO | WO 97/46230 | 12/1997 |
| WO | WO 98/05318 | 2/1998 |
| WO | WO 98/49129 | 11/1998 |

OTHER PUBLICATIONS

Kawamura et al. Hypertension 1996, 27, 408-413 (pp. 1 to 12 printed).*
Derwent-Acc-No. 1988-087068 abstacting JP 63036744A 2 pages.*
Alonso et al. (J. Dairy Sci. 2003, 86, 1941-1946).*
Langer, Clin. and Exper. Hypertension, 17(7):1127-44 (1995).
Hennekens, Am. J. Medicine, 104(6A):50S-53S (1998).
Black, JAMA, 270(6):757-59 (1993).
Tietz et al., Clin. Chem. 39(5):746-56 (1993).
Thompson, Brit. Med. Bull. 46(4):986-1004 (1994).
U.S. Appl. No. 09/160,416.
U.S. Appl. No. 09/270,941.
Tonstad et al., Eur. J. Clin. Pharmacol. 46:405-10 (1994).
Chin et al., J. Food Comp. Anal. 5: 185-197 (1992).
Belury, Nut. Rev. 53(4): 83-9 (1995).
Cowan, JAOCS 72:492-99 (1950).
Marcel and Mustafa, Lipids, 32 (10) 1019-34 (1997).
Scholfield and Koritalia, "A Simple Method for Preparation of Methyl trans-10,cis-12 Octadecadienoate," JOACS 47(8):303 (1970).
Sugano et al., "Conjugated Linoleic Acid Modulates Tissue Levels of Chemical Mediators and Immunoglobulins in Rats," Lipids, 33(5):521-27 (1998).
Matreya Catalog, 1997, pp. 33-34.
Hudtwalcker & Co. AS Technical Data Sheet, exact publication date unknown, describes CLA compositions with various levels of CLA.
Selin CLA Product Literature, Jan. 1997, describes triglycerides incorporating CLA.
Lipid Technology Newsletter, Peter J. Barnes, Ed., vol. 4, No. 5, pp. 85-86 (Oct. 1998).
Natural Lipids Ltd. AS Technical Data Sheet, Jan. 20, 1997.
Ron Udell, Information About Conjugated Linoleic Acid, published by Soft Gel Technologies Incorporated.

* cited by examiner

*Primary Examiner* — Ernst Arnold
(74) *Attorney, Agent, or Firm* — Casimir Jones, S.C.

(57) ABSTRACT

This invention relates to a method of treating hypertension and reducing serum lipase activity by dietary supplementation with conjugated linoleic acid. The method comprises administering a safe and effective amount of conjugated linoleic acid to a human. The conjugated linoleic acid may be provided in the form of a free fatty acid or chemical derivatives thereof in a pill, or as a component of a prepared food product.

5 Claims, No Drawings

METHOD OF TREATING HYPERTENSION AND REDUCING SERUM LIPASE ACTIVITY

FIELD OF THE INVENTION

This invention relates to a method of treating hypertension and reducing serum lipase activity by dietary supplementation with conjugated linoleic acid.

BACKGROUND

1. Hypertension

Antihypertensive therapy has been available for more than 40 years to reduce blood pressure and to prevent morbidity and mortality related to the hypertensive state. Hypertension is generally defined as an abnormally increased blood pressure. It is clinically recognized as an elevation of systolic arterial blood pressure of 150 mm Hg or greater and/or an elevation of diastolic arterial blood pressure of 90 mm Hg or higher. Certain risk factors (e.g., hypercholesterolemia, diabetes, smoking, and a familial history of vascular disease) in conjunction with hypertension may predispose individuals to arteriosclerosis and consequent cardiovascular morbidity and morality.

Data which demonstrates that there is a linear relationship between elevated blood pressure and adverse cardiovascular events has led to the identification of an at risk group with "mild" or stage 1 hypertension. Mild hypertension is defined as a systolic blood pressure of 140-159 mmHg or diastolic blood pressure of 90-99 mmHg. These levels move the definition of hypertension towards the populations mean, effectively doubling the prevalence of hypertension in the U.S. Langer, Clin. and Exper. Hypertension, 17(7):1127-44 (1995). Of the 25% of the U.S. population affected by hypertension under this definition, greater than 60% have mild hypertension.

Prospective observational studies indicate that a prolonged difference of 5-6 mmHg in usual diastolic blood pressure (DBP) is related to differences of approximately 35-40% in the risk of stroke and 20-25% in the risk of cardiovascular disease. Hennekens, Am. J. Medicine, 104(6A):50S-53S (1998). Therefore, it appears that treatment of mild hypertension with drugs would be indicated in a majority of cases. However, the literature indicates that doubt remains as to whether the benefits of utilizing expensive diuretics and n-blockers to treat mild hypertension outweighs the risk, and whether lifestyle changes in physical activity and diet are as effective as drugs and potentially safer. Black, JAMA, 270 (6):757-59 (1993). These differences are highlighted by the fact that the Joint National Committee guidelines advises routine treatment of patients with a sustained elevated blood pressure of over 140/90 mmHg, while the British Hypertension Society guidelines advise treatment at 160/100 mmHg. Ransay et al., Am. J. Hypertension 11(6 pt 2):79S-88S (1998). Such concerns may contribute to a hesitancy on the part of some physicians to prescribe drugs to treat mild hypertension.

Several types of anti-hypertensive drugs are known. β-blockers are antagonists of the β-adrenoreceptor and include such drugs as acebutalol, propranolol and timolol. Calcium antagonists including phenylalkylamines, benzothiazepines and dihydropyridines have been shown to reduce blood pressure. Angiotensin Converting Enzyme (ACE) inhibitors which have been used to treat hypertension include captopril and enalapril. Diuretic agents have also become a mainstay in anti-hypertensive therapy, and include thiazides and closely related phthalimidine derivatives (e.g., chlorthalidone).

In general, however, drug therapy for hypertension is reserved for those individuals whose blood pressure cannot be maintained in an acceptable range by non-pharmacological means. Each of the above described methods depends on prescription medications. Of the non-pharmacological treatments for hypertension, weight reduction and salt (sodium chloride) restriction have been considered to be the most successful. Restricting dietary salt, although of somewhat limited and unpredictable effect, can in some cases reduce diastolic blood pressure to an extent comparable to that achieved by treatment with some of the pharmacologic agents.

2. Serum Lipase Activity

Serum lipase is mainly derived from the pancreatic acinar cells, where it is synthesized and stored in granules. The majority of lipase is secreted into the ductal system of the pancreas, with less than 1% diffusing from the acinar cells into the lymphatics and capillaries where it reached the general circulation system. High levels of serum lipase activity are used as a clinical indicator of pancreatitis as described in Tietz et al., Clin. Chem. 39(5):746-56 (1993), incorporated herein by reference. Reduction of lipase activity may be of use in treating the disease hyperlipidaemia, which is reviewed in Thompson, Brit. Med. Bull. 46(4):986-1004 (1994), incorporated herein by reference. Inhibition of pancreatic lipase prevents hydrolysis of triglycerides, thereby reducing triglyceride absorption and the amount of free fatty acids and monoglycerides in the intestine. Tonstad et al., Eur. J. Clin. Pharmacol. 46:405-10 (1994), incorporated herein by reference.

What is needed is a safe, cheap and effective substance for reducing blood pressure in patients with mild hypertension and for reducing serum lipase activity. Preferably the substance should be naturally occurring and should be able to be made part of a healthy every day diet.

SUMMARY OF THE INVENTION

An important challenge in modern medicine is to devise safe and effective methods of treating mild hypertension. This invention relates to methods of treating hypertension and reducing serum lipase activity by dietary supplementation with conjugated linoleic acid.

In some embodiments of the present invention, a method of treating hypertension in a subject is provided, comprising a) providing a subject and a composition comprising a safe and effective amount conjugated linoleic acid; and b) administering the conjugated linoleic acid composition to the subject under conditions such that blood pressure of the subject is reduced. The present invention is not limited to any particular conjugated linoleic acid composition. Indeed, a variety of conjugated linoleic acid compositions are contemplated including, but not limited to, pills, capsules, tablets, food products, esters (e.g., methyl and ethyl esters), and triglycerides. In other embodiments, the CLA composition includes a mixture of the eight possible isomers cis-9, trans-11; cis-9, cis-11; trans-9, cis-11; trans-9, trans-11; cis-10, cis-12; cis-10, trans-12; trans-10, cis-12, and trans-10, trans-12 octadecadienoic acids. In other embodiments, the mixture is a more purified mixture consisting of predominantly the cis-9, trans-11 and trans-10, cis-12 isomers, or simply the cis-9, trans-11 or trans-10, cis-12 isomer alone.

The present invention is not limited to any particular dose of CLA. Indeed, the administration of a variety of amounts of CLA is contemplated. In some embodiments, a safe and effective amount of CLA is administered. In other embodiments, a daily dosage of between 0.1 and 12 grams, preferably about 4.5 grams is administered. In some embodiments, the CLA is administered in a single dose. In other embodiments, the CLA is administered in 2, 3, 4, or more doses throughout a 24 hour period.

The present invention is not limited to any particular subject. Indeed a variety of subjects are contemplated, including, but not limited to, animals, mammals, humans, cows, pigs, goats, horses, dogs, cats, and sheep. In some embodiments, the subject is diagnosed as suffering from hypertension. In other embodiments, the subject suffers from mild hypertension. In still further embodiments, the CLA composition is administered prophylactically to a subject with one or more of the following risk factors for developing hypertension (e.g., hypercholesterolemia, diabetes, smoking, family history of diabetes).

In still further embodiments of the present invention, a method of reducing serum lipase activity in a subject is provided, comprising a) providing a subject and a composition comprising a safe and effective amount conjugated linoleic acid; and b) administering the conjugated linoleic acid composition to the subject under conditions such that serum lipase activity of the subject is reduced. The present invention is not limited to any particular conjugated linoleic acid composition. Indeed, a variety of conjugated linoleic acid compositions are contemplated including, but not limited to, pills, capsules, tablets, food products, esters (e.g., methyl and ethyl esters), and triglycerides. In other embodiments, the CLA composition includes a mixture of the eight possible isomers cis-9, trans-11; cis-9, cis-11; trans-9, cis-11; trans-9, trans-11; cis-10, cis-12; cis-10, trans-12; trans-10, cis-12, and trans-10, trans-12 octadecadienoic acids. In other embodiments, the mixture is a more purified mixture consisting of predominantly the cis-9, trans-11 and trans-10, cis-12 isomers, or simply the cis-9, trans-11 or trans-10, cis-12 isomer alone.

The present invention is not limited to any particular dose of CLA. Indeed, the administration of a variety of amounts of CLA is contemplated. In some embodiments, a safe and effective amount of CLA is administered. In other embodiments, a daily dosage of between 0.1 and 12 grams, preferably about 4.5 grams is administered. In some embodiments, the CLA is administered in a single dose. In other embodiments, the CLA is administered in 2, 3, 4, or more doses throughout a 24 hour period.

The present invention is not limited to any particular subject. Indeed a variety of subjects are contemplated, including, but not limited to, animals, mammals, humans, cows, pigs, goats, horses, dogs, cats, and sheep. In some embodiments, the subject is diagnosed as having elevated serum lipase activity as compared to population norms or as having pancreatitis. In other embodiments, the CLA composition is administered prophylactically to a subject at risk of developing hyperlipidemia.

Dietary supplementation with CLA presents an effective treatment for hypertension or the reduction of serum lipase activity, and may be used alone or in combination with other treatment regimes.

DEFINITIONS

To facilitate understanding of the invention, a number of terms are defined below.

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11, 13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "conjugated linoleic acid composition" refers to any material containing conjugated linoleic acid or a derivative of CLA (e.g., a triglyceride of CLA or ester of CLA) including, but not limited to, pills, capsules, tablets, food products, etc.

As used herein, it is intended that "triglycerides" of CLA contain CLA at any or all of three positions (i.e., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,c10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

"Prepared food product" means any pre-packaged food approved for human consumption.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed).

As used herein the term "subject" refers to a animal, either human or otherwise, that can be treated either therapeutically or prophylactically with CLA compositions.

As used herein, the term "safe and effective amount conjugated linoleic acid" refers to the amount CLA that, when ingested in purified form or as food supplement results in a reduction blood pressure or serum lipase activity without impairing or interfering with proper nutrition.

As used herein, the term "under conditions such that blood pressure is reduced" refers to a measurable decrease in blood pressure measured by means known in the art.

As used herein, the term "under conditions such that serum lipase activity is reduced" refers to a measurable decrease in serum lipase activity as measured by assays known in the art.

DESCRIPTION OF THE INVENTION

Conjugated linoleic acid (CLA, also known as octadecadienoic acid), has been identified in meat and dairy products by Chin et al., *J. Food Comp. Anal.* 5: 185-197 (1992). CLA is a collective term for positional and geometric isomers of linoleic acid with conjugated double bonds at carbon atoms 10 and 12 or 9 and 11 in the various cis-trans conformations. CLA differs from ordinary linoleic acid which has double bonds at carbon atoms 9 and 12.

CLA has several unique properties when used as a food additive or dietary supplement. U.S. Pat. No. 5,554,646 (herein incorporated by reference) discloses the use of CLA to reduce the percentage of fat in relation to total body mass. U.S. Pat. No. 5,428,072 (herein incorporated by reference) discloses the use of CLA for increasing the efficiency of feed conversion in animals, which results in more non-fat tissue being formed in relation to weight gain. U.S. Pat. Nos. 5,430,066 and 5,585,400 (herein incorporated by reference) disclose the use of CLA to prevent weight loss due to immune stimulation and to treat immune hypersensitivity. CLA also has anticarcinogenic activity, as shown in Belury, Nut. Rev. 53(4): 83-9 (1995). Therefore, CLA may be used for increasing or maintaining weight gain in animals.

The mechanism by which CLA mediates these effects is not known, although some biochemical models involving fat partitioning and shifts in fatty acid precursor mediated synthesis of end product prostaglandins and leukotrienes have been proposed. It is known that CLA is taken up in triglycerides and phospholipids, and deposited in fat stores. The precise structure and distribution of these lipids is not known. Nor is it known whether there is a competitive incorporation amongst two or more isomers, or a preferential deposition of certain isomers in some lipid species over others.

The CLA of the present invention is preferably a mixture of one or all of the isomers of octadecadienoic acid including the cis-9, trans-11; cis-9, cis-11; trans-9, cis-11; trans-9, trans-11; cis-10, cis-12; cis-10, trans-12; trans-10, cis-12; and trans-10, trans-12 isomers. The rearrangement of the double bonds of linoleic acid to conjugated positions has been shown to occur during treatment with catalysts such as nickel or alkali at high temperatures, and during auto oxidation. Theoretically, eight possible geometric isomers of 9,11 and 10,12 octadecadienoic acid ($c9,c11$; $c9,t11$; $t9,c11$; $t9,t11$; $c10,c12$; $c10,t12$; $t10,c12$ and $t10,t12$) would form from the isomerization of $c9,c12$-octadecadienoic acid.

A general mechanism for the isomerization of linoleic acid was described by J. C. Cowan in *JAOCS* 72:492-99 (1950). It is believed that the double bond is polarized by the result of a collision with an activating catalyst. The polarized carbon atom and its adjoining carbon are then free to rotate and the forces are such as to make the deficient carbon atom essentially planar. When the system then moves to relieve these forces set up as a result of the collision, both cis and trans isomers are formed. The formation of certain isomers of CLA is thermodynamically favored. This is due to the co-planar characteristics of the five carbon atoms around the conjugated double bond and a spatial conflict of the resonance radical.

The relatively higher distribution of 9,11 and 10,12 isomers apparently results from the further stabilization of the $c9, t11$ or $t10, c12$ geometric isomers. The present invention is not limited to any particular mechanism of action. Indeed, an understanding of the mechanism of action is not needed in order to practice the present invention. However, it is contemplated that the cis-9,trans-11 and trans-10, cis-12 isomers are thought to have the most biological activity. Therefore, these isomers may be used in a purified form or CLA compositions which contain high ratios of these isomers may be utilized. Most preferably, the CLA composition used in the present method is CLA 80 and is available from Natural Nutrition, Norway. Methods for manufacturing CLA useful in the present invention are provided in Example 2 (low temperature nonaqueous alkali isomerization) and an alternative method of manufacturing another preferred CLA composition is provided in Example 3 (isomerization with alkali alcoholate in the presence of a monohydric low molecular weight alcohol). Both methods provide for the production of CLA predominantly comprising the $c9,t11$- and $t10,c12$- isomers, with low levels of 8,10-,11,13- and trans-trans isomers.

In the preferred embodiment of the present invention, a safe and effective amount of CLA is orally administered to a human to treat mild hypertension (e.g., reduce blood pressure) or to reduce serum lipase activity. The use of CLA for these indications is desirable because CLA is a non-toxic, naturally occurring food ingredient. CLA is not a drug and may be consumed as a part of a normal diet and finds use as a part of everyday nutrition.

The data described below in Example 1 indicates that dietary supplementation with CLA results in a decrease in both systolic and diastolic blood pressure in humans with borderline mild hypertension. Studies have shown that decreases of from 5-6 mmHg in diastolic blood pressure are related to differences of approximately 35-40% in the risk of stroke and 20-25% in the risk of cardiovascular disease. Hennekens, Am. J. Medicine, 104(6A):50S-53S (1998). The effect of reducing blood pressure is known to be linear. Langer, Clin. and Exper. Hypertension, 17(7):1127-44 (1995). Therefore, the reduction of blood pressure due to the dietary administration of CLA will have a positive impact in the reduction of stroke and cardiovascular disease.

The safe and effective amount of CLA is also sufficient to cause a decrease in serum lipase activity as compared to the controls (See, Example 2). This will positively effect overall lipid metabolism, resulting in decreased triglyceride adsorption and a decrease in the amount of free fatty acids and monoglycerides in the intestine. This effect will also be useful in the treatment of hyperlipidaemia in overweight patients, and in the reduction of metabolized plasmid lipids such as free fatty acids and monoglycerides in otherwise healthy patients, leading to improved cardiovascular health. The present invention is not limited to any particular mechanism. Indeed, an understanding of the mechanism is not required to practice the present invention. However, it is contemplated that triglycerides containing CLA isomers will be especially desirable for regulating serum lipase activity. The lipase will hydrolyze the triglyceride to release the CLA isomers as free fatty acids, which results in down regulation of lipase activity by a feed-back loop mechanism. As the free CLA isomers are further metabolized, thereby reducing their effective concentration, lipase activity will increase, causing the release of more CLA isomers from the triglyceride.

A safe and effective amount is that amount CLA that, when ingested in purified form or as food supplement results in a reduction blood pressure or serum lipase activity without impairing or interfering with proper nutrition. About 0.1 to 20 grams of CLA may be administered per day, preferably about 1 to 10 grams per day may be administered and most preferably about 4.5 grams per day may be administered. In general, the amount of CLA administered is not critical as long as it is enough to be therapeutically effective. The amounts of CLA deemed therapeutically effective are those which result in a measurable decrease in blood pressure or serum lipase activity when administered over a three month period or longer.

In a typical regimen, an individual will begin the hypertension treatment program or serum lipase activity reduction program by ingesting up to several grams (e.g., 0.1 to 5 grams) of CLA with each meal, and monitoring blood pressure over a period of several months. The CLA may be provided in the form of a pill or as a component of a prepared food product. Once the desired blood pressure or serum lipase activity has been attained, a proper maintenance level can be found by gradually reducing the dose and continuing to monitor blood pressure to assure there is no increase.

It is anticipated that there will be some variation in effectiveness because of differences among individuals in parameters such as body weight, basal metabolism, exercise, and other aspects of the diet. The individual should begin with the preferred 4.5 gram dose for an initial two month period, and then, if no reduction in blood pressure or serum lipase activity is experienced, gradually increase the CLA dose up to about 10-20 grams per day.

Derivatives of CLA may also be utilized in the present invention. The CLA may be free or bound through ester linkages. For example, the CLA may be provided in the form of an oil containing CLA triglycerides (See, e.g., U.S. application Ser. Nos. 09/160,416 and 09/270,941, each incorporated herein by reference). The triglycerides may be partially or wholly comprised of CLA attached to a glycerol backbone. Furthermore, the CLA may be in the form of a non-toxic salt, such as a potassium or sodium salt, which is formed by reacting chemically equivalent amounts of the free acids with an alkali hydroxide at a pH of about 8 to 9. The CLA may also be used in liquid, gel or powdered forms.

The preferred method of administration is oral. The CLA may be formulated with suitable carriers such as starch, sucrose or lactose in tablets, capsules, solutions and emulsions. The tablet or capsule of the present invention may be coated with an enteric coating which dissolves at a pH of about 6.0 to 7.0. A suitable enteric coating which dissolves in the small intestine but not in the stomach is cellulose acetate phthalate.

A safe and effective amount of CLA may also be provided as a supplement in various prepared food products. For the purposes of this application, prepared food product means any natural, processed, diet or non-diet food product to which CLA has been added. The CLA may be added in the form of free fatty acids or as an oil containing partial or whole triglycerides of CLA. Therefore, CLA may be directly incorporated into many prepared diet food products, including, but not limited to diet drinks, diet bars and prepared frozen meals. Furthermore, CLA may be incorporated into many prepared non-diet products, including, but not limited to candy, snack products such as chips, prepared meat products, milk, cheese, yogurt and any other fat or oil containing foods.

CLA is also susceptible to oxidation. Therefore it is desirable to package CLA for human use with suitable antioxidants such as lecithin, tocopherols, ascorbate, ascorbyl palmitate, or spice extracts such as rosemary extract.

EXPERIMENTAL

The following examples are provided in order to demonstrate and further illustrate certain preferred embodiments and aspects of the present invention and are not to be read as limiting the scope thereof.

Example 1

Effect of CLA on Lowering Blood Pressure

This example demonstrates the effectiveness of CLA administration for the reduction of blood pressure. Fifty patients were divided into a control group receiving a placebo (25 patients, olive oil, two 750 mg capsules taken before each meal for a total of 4.5 g/day) and a treatment group receiving conjugated linoleic acid (25 patients, CLA 80, Natural Lipids, Norway, two 750 mg capsules taken before each meal, for a total of six a day). The blood pressure of each patient was measured at the start of the study (visit 1), after 6 weeks (visit 2), and after 12 weeks (visit 3). Dietary supplementation with CLA resulted in a decrease in both systolic and diastolic pressure. The decrease was greater than that observed in the control group. The results are summarized in Table 1.

TABLE 1

| Pressure (mmHg) | Control Group | | Treatment Group | |
| --- | --- | --- | --- | --- |
| | Systolic | Diastolic | Systolic | Diastolic |
| Visit 1 | 131.96 | 82.28 | 146.32 | 90.44 |
| Visit 2 | 132.28 | 81.12 | 145.24 | 88.36 |
| Visit 3 | 129.48 | 81.60 | 142.48 | 87.52 |

Example 2

CLA Reduces Serum Lipase Activity

This example demonstrates the effectiveness of CLA administration for the reduction of serum lipase activity. Fifty patients were divided into a control group receiving a placebo (25 patients, olive oil, two 750 mg capsules taken before each meal for a total of 4.5 g/day) and a treatment group receiving conjugated linoleic acid (25 patients, CLA 80, Natural Lipids, Norway, two 750 mg capsules taken before each meal, for a total of six a day). The serum lipase activity of each patient was measured at the start of the study (visit 1) and after 12 weeks (visit 3). Dietary supplementation with CLA resulted in a decrease in serum lipase activity. This is in contrast to the increase in serum lipase activity observed in the control group. The results are summarized in Table 2.

TABLE 2

| | Serum Lipase Activity | |
| --- | --- | --- |
| | Control Group | Treatment Group |
| Visit 1 | 70.79 | 97.56 |
| Visit 3 | 79.2 | 77.5 |

Example 3

Isomerization of Safflower Oil Using Propylene Glycol at Low Temperature

This example describes the preparation of CLA. Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 µl of purified water in a new test tube and again shaken under nitrogen. The resulting upper layer was then washed of isooctane and decanted into a third test tube. A small amount of sodium sulfate was added for water absorption. A 1 µl sample was then injected directly into the Gas chromatograph.

The gas chromatography conditions were as follows:

| System: | Perkins-Elder Auto System |
| --- | --- |
| Injector: | Splitless at 240° C. |
| Detector: | Flame Ionization Detector at 280° C. |
| Carrier: | Helium |
| Column: | WCOT Fused Silica 0.25 mm X100M, CP-SL 88 for FAME, DF 0.2 |
| Oven Program: | 80° C. (0 min.) increasing to 220° C. at 10° C. per min. and held at 220° C. for 10 min. |

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, Lipids, 32 (10) 1019-34 (1997), incorporated herein by reference.

The GC data demonstrated that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just before the c9,t11 isomer. The 11,13 isomer elutes in front of the t10,c11 isomer or coelutes with the t10,c12 isomer, depending on the column conditions. The GC results are summarized in Table 3.

The conjugated linoleic acid produced according to this method by characterized by comparing the various isomers produced. First, the isomerization reaction went essentially to completion. The completeness of the reaction is obtained by dividing the total peak area the for linoleic acid isomers minus residual c9, t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018.

A high percentage of linoleic acid is converted primarily to the conjugated c9,t11 and t10,c12 isomers in a carefully controlled reaction yielding greater than 90 percent of these isomers, so that less than a combined 1 percent of the 11,13 isomers, less than 1 percent of the 8,10 isomers, less than 1 percent of the double trans species (the t9,t11 and t10,t12 isomers), and less than 1 percent total unidentified linoleic acid species is present in contrast to conventional compositions. The predominance of the c9,t11- and c10,t12- isomers in this composition may contribute to its biological effect. In many individual product runs, the final composition has levels of these species virtually undetectable by GC analysis. The 1 percent limit in concentration of the 11,13 and 8,10 isomers serves as a convenient and practical quality assurance standard of purity for a commercial scale manufactured food grade product.

TABLE 3

GC Analysis

| Peak # | Time (Min) | Component Name | Area (%) | Area (µV · s) | Height (µV) |
| --- | --- | --- | --- | --- | --- |
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9, c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9, t11 | 36.51 | 1950669.98 | 124313.83 |
| 15 | 78.370 | CLA t10, c12 | 37.16 | 1985488.96 | 132265.33 |
| 16 | 78.664 | CLA c9, c11 | 1.06 | 56583.10 | 5699.43 |
| 17 | 78.880 | CLA c10, c12 | 1.26 | 67503.55 | 4572.65 |
| 18 | 80.102 | CLA t9, t11/ t10, t12 | 0.73 | 39110.00 | 4743.28 |
| 19 | 85.165 | | 0.03 | 1621.65 | 231.32 |
| Total | | | 100.00 | 5343381.15 | 384147.01 |

Example 4

Large Scale Batch Production of Conjugated Safflower FAME

This example describes the synthesis of CLA methyl esters. The technique may be adapted as is known in the art for the production of ethyl esters of CLA. The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30% solution) were added. The mixture is heated to 65° C. while stirring, and reacted at 65° C. for 2 hours. The resulting bottom layer was decanted while the reactor was purged with nitrogen gas. 1000 liters of water (40-50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of $KOCH_3$ dissolved in methanol to form a paste was added to the reactor. The mixture was then heated to 120° C. while stirring and the reaction allowed to continue for 3 hours. The mixture was cooled to 100° C., and 1000 liters of water (40-50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

| Column: | WCOT Fused Silica 100 m X 0.25 mm, Coating CSIL 88 |
| --- | --- |
| Carrier: | He gas, 30.0 PSI |
| Temp: | 220 C. |
| Run time: | 35-90 min. |
| Inject.: | Splitless, 240 C. |
| Detect.: | FID, 280 C. |

The GC results are summarized in Table 4.

TABLE 4

| GC Results | | | | | |
| --- | --- | --- | --- | --- | --- |
| Peak # | Time (min) | Component Name | Area (%) | Area (µVs) | Height (µV) |
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 |  | 0.70 | 3263.62 | 391.92 |
| 5 | 66.404 |  | 0.35 | 1627.60 | 177.41 |
| 6 | 66.917 |  | 0.26 | 1239.15 | 157.35 |
| 7 | 67.583 | C18:2 c9, c12 | 5.75 | 26964.95 | 3153.80 |
| 8 | 70.631 |  | 0.25 | 1171.90 | 141.41 |
| 9 | 75.011 | CLA | 34.42 | 161529.90 | 17544.79 |
| 10 | 75.936 | CLA c9, t11 t10, c12 | 33.48 | 157129.82 | 17157.21 |
| 11 | 76.400 | CLA c9, c11 | 0.84 | 3935.70 | 302.61 |
| 12 | 76.631 | CLA c10, c12 | 0.49 | 2316.98 | 279.31 |
| 13 | 77.905 | CLA t, t 9, 11 + 10, 12 | 1.35 | 6344.50 | 710.88 |
| Total | | | 100.00 | 469299.10 | 52954.41 |

What should be clear from above is that the present invention provides compositions and methods for reducing blood pressure and serum lipase activity in subjects. The compositions contain naturally occurring isomers of conjugated linoleic acid and do not require a prescription for use.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

What is claimed is:

1. A method of treating hypertension in humans comprising:
   a) providing a hypertensive human patient in need of hypertension treatment and a composition comprising a safe and effective amount conjugated linoleic acid for treating hypertension; and
   b) administering said conjugated linoleic acid composition to said human patient so that blood pressure of said human patient is reduced.

2. The method of claim 1 wherein the conjugated linoleic acid composition is a mixture of octadecadienoic acid isomers selected from the group of cis-9, trans-11; cis-9, cis-11; trans-9, cis-11; trans-9, trans-11; cis-10, cis-12; cis-10, trans-12; trans-10, cis-12; trans-10, trans-12 octadecadienoic acid.

3. The method of claim 1 wherein the conjugated linoleic acid composition consists essentially of octadecadienoic acid isomers selected from 9,11 octadecadienoic acid, 10,12 octadecadienoic acid, and mixtures thereof.

4. The method of claim 1 wherein the conjugated linoleic acid is administered orally.

5. The method of claim 1 wherein said safe and effective amount of conjugated linoleic acid is about 0.1 grams to 20 grams.

* * * * *